US00PP36770P2

(12) United States Plant Patent
Steffen

(10) Patent No.: US PP36,770 P2
(45) Date of Patent: Jun. 24, 2025

(54) ***ANGELONIA* PLANT NAMED 'ANGAF19273'**

(50) Latin Name: *Angelonia hybrida*
Varietal Denomination: ANGAF19273

(71) Applicant: Elsner pac Vertriebsgesellschaft mbH Berlin, Thiendorf (DE)

(72) Inventor: Elke Steffen, Erfurt (DE)

(73) Assignee: Elsner pac Vertriebsgesellschaft mbH Berlin, Thiendorf (DE)

( * ) Notice: Subject to any disclaimer, the term of this patent is extended or adjusted under 35 U.S.C. 154(b) by 0 days.

(21) Appl. No.: 18/773,047

(22) Filed: Jul. 15, 2024

(51) Int. Cl.
*A01H 5/02* (2018.01)
*A01H 6/68* (2018.01)

(52) U.S. Cl.
USPC ..... Plt./404
CPC ..... *A01H 6/68* (2018.05)

(58) Field of Classification Search
USPC ..... Plt./404
CPC ..... A01H 5/02
See application file for complete search history.

*Primary Examiner* — Kent L Bell
(74) *Attorney, Agent, or Firm* — The Webb Law Firm

(57) ABSTRACT

A new and distinct freely flowering *Angelonia* plant with bicolored pink and white flowers.

1 Drawing Sheet

Botanical classification: *Angelonia hybrida.*
Varietal denomination: 'ANGAF19273'.

BACKGROUND OF THE INVENTION

The present invention comprises a new and distinct variety of *Angelonia hybrida* known by the varietal name 'ANGAF19273'. The new variety was discovered in August of 2019 in a planned breeding program in Dresden, Germany. The purposes of the breeding program were to develop freely flowering plants that are suitable for containers. The new variety is the result of a cross between an unpatented *Angelonia hybrida* variety having an internal breeder's reference of "AN-17075" (female parent) and pollination from a group of unpatented *Angelonia hybrida* plants from the breeder's own collection. As such, the exact male parent from this collection is unknown. The new variety was first asexually reproduced in January of 2020 by terminal cuttings in Thiendorf, Germany. The new variety has been trial and field tested in Thiendorf, Germany and has been found to retain its distinctive characteristics and remain true to type through successive asexual propagations.

The new variety is similar to its female parent in having bicolored pink and white flowers, but has a more stable flower pattern than its female parent. The new variety is similar to *Angelonia* variety named "ALONIA™ Big Bicolor Pink Improved" (believed to be unpatented) in having bicolored pink and white flowers, but the pink flower color of the comparison variety is slightly lavender pink and the pink flower color the new variety is a rose pink. The following characteristics further distinguish the new variety from other *Angelonia* varieties known to the breeder:

Bicolored bright pink and white flowers; and
Clear contrast of the colors of the flowers.

DESCRIPTION OF THE DRAWING

The accompanying photographic drawing, FIG. 1, illustrates the new variety at 16 weeks of age, with the color being as nearly true as is possible with color illustrations of this type.

DESCRIPTION OF THE PLANT

The following detailed description sets forth the characteristics of the new cultivar. The data that defines these characteristics were collected by asexual reproductions carried out in a greenhouse in Thiendorf, Germany on plants at 20 weeks of age that were grown in approximately 25.0 cm diameter pots. The color readings were taken on a plant indoors under natural light. Color references are primarily to the 1995 edition of The R.H.S. Colour Chart of The Royal Horticultural Society of London, except where terms of ordinary color significance are used.

PLANT

Form: Broadly upright.
Height (from soil): 30.0-50.0 cm to top of foliage, 40.0-80.0 cm to top of flowers.
Diameter: 30.0 cm.
Growth: Well-branched from the base with a moderate vigor.
Time to initiate roots: About 10-14 days at 20° C.
Time to develop roots: About 21-28 days at 20° C.
Rooting habit: Fine, fibrous, and of medium density.
Root color: 156D while young.
Disease/pest resistance/susceptibility: Nothing unusual noted to date.
Weather tolerance: Good rain tolerance.
Seed/fruit production: Present.
Main stem:
- *Form.*—Upright and slightly rectangular in cross section.
- *Color.*—144B.
- *Texture.*—Slightly pubescent.
- *Length.*—Approximately 80.0 cm.
- *Diameter.*—2.0-4.0 cm.
- *Internode length.*—0.5-2.5 cm.

Lateral branches:
- *Form.*—Upright and slightly rectangular in cross section.
- *Color.*—144B.

*Texture*.—Slightly pubescent.
*Length*.—Up to 70.0 cm.
*Diameter*.—Up to 4.0 cm.
*Internode length*.—Up to 2.5 cm.

Foliage:
*Arrangement* (*e.g., alternate, single*).—Opposite, decussate, simple sessile.
*Number of leaves per branch*.—About 30-50.
*Size of leaf*.—Length: 4.0-9.0 cm. Width: 1.0-2.0 cm.
*Shape of leaf* (*generally*).—Lanceolate.
*Shape of apex*.—Acute.
*Shape of base*.—Attenuate.
*Texture*.—Smooth and shiny adaxially, scabrous and matte abaxially.
*Margin type*.—Serrate.
*Color*.—Young leaves: Upper surface: Close to 137A. Lower surface: Close to 137B. Mature leaves: Upper surface: Close to 147A. Lower surface: Close to 147B.
*Petiole*.—Not present.
*Veins*.—Venation type: Longitudinal. Color: Upper surface: Close to 147A. Lower surface: Close to 147B.

FLOWER

Natural flowering season at specified location(s): From spring to autumn in central Europe.
Flower type and habit: Single flowers arranged in upright, terminal racemes.
Number of flowers per plant: From 50-200.
Typical number of flowers per inflorescence: About 10.

Bud (described shortly before opening):
*Shape*.—Globose.
*Diameter*.—10.0 mm.
*Length*.—8.0 mm.
*Color*.—150A.

Inflorescence:
*Length*.—10-50 cm.
*Diameter*.—7-9 cm.
*Longevity*.—Inflorescences are indeterminate and continue growing throughout the season.

Flower:
*Shape*.—Two-lipped corolla with a dotted saccate throat merging into a very short funnel-shaped tube. The transition between tube and throat is gradual. Five lobes, with the two upper lobes typically reflexed. The upper lip sometimes has one or two additional lobes. Slightly bisymmetrical calyx with five lobes.
*Diameter*.—22.0-28.0 mm.
*Length*.—Approximately 5.0 mm.
*Fragrance*.—Faint, delicate scent.
*Lasting quality*.—Typically one week, can be up to two weeks.

Corolla lobes:
*Shape*.—Reniform, lowest lobe with concave palate at base.
*Apex*.—Round.
*Base*.—Connate.
*Margin*.—Crenulate.
*Texture*.—Smooth adaxial surface and slightly waxy abaxial surface.

Color of upper lobes:
*When opening*.—Upper surface: 63C to 63D. Lower surface: 63D.
*Fully opened*.—Upper surface: 63C to 63D. Lower surface: 63D.

Color of median lobes:
*When opening*.—Upper surface: 63C to 63D and 155A at the margin. Lower surface: 63D and 155A at the margin.
*Fully opened*.—Upper surface: 63C to 63D and 155D at the margin. Lower surface: 63D and 155D at the margin.

Color of the lowest lobe:
*When opening*.—Upper surface: 155A and 65C in the center. Lower surface: 155A and 65D in the center.
*Fully opened*.—Upper surface: 155A and 65C in the center. Lower surface: 155A and 65D in the center.

Corolla throat:
*Diameter*.—6-7 mmm.
*Depth*.—*About* 5.0 mm.
*Texture*.—Smooth on inner and outer side.
*Color inside throat*.—155A to 65C with dots in 71A-72A.
*Color outside throat*.—155A to 65C with dots in 71A-72A.

Corolla tube:
*Diameter*.—About 1 mm at base.
*Length*.—About 1-3 mm.
*Texture*.—Smooth on inner and outer side.
*Color inside tube*.—145C to 65B.
*Color outside tube*.—145C to 65B.

Sepals:
*Number*.—5.
*Length*.—4.0-5.0 mm.
*Width*.—2.0 mm.
*Shape*.—Ovate.
*Apex*.—Acute.
*Base*.—Basally connate.
*Margin*.—Entire.
*Color*.—143A (identical on both sides of the sepal).
*Texture*.—Adaxially pubescent and abaxially smooth.

Peduncle: Not present.

Pedicel:
*Length*.—12.0-25.0 mm.
*Diameter*.—1.0 mm or less.
*Color*.—145B to 177B.
*Texture*.—Pubescent.
*Strength*.—Moderate.
*Angle*.—Pedicels sit at a more or less right angle on the stem.

REPRODUCTIVE ORGANS

Stamens:
*Number* (*per flower*).—4.
*Filament length*.—Approximately 5.0 mm.
*Filament color*.—155D.
*Anthers*.—Shape: Elliptic. Length: 1.0-2.0 mm. Color: 155A to 66C.
*Pollen*.—Color: 158A. Amount: Moderate.

Pistils:
*Number* (*per flower*).—1.
*Length*.—5.0-6.0 mm.
*Style*.—Length: 3.0 mm. Color: 158A.

*Ovary*.—Length: 2.0-3.0 mm. Color: 155D to 145B.

*Stigma*.—Shape: Punctiform. Color: 155D.

Fruit:

*Shape*.—Globular.

*Length*.—About 4 mm.

*Diameter*.—About 4 mm.

*Color*.—164D.

Seed:

*Shape*.—Prismatic.

*Length*.—Less than 1 mm.

*Diameter*.—Less than 1 mm.

*Color*.—164B.

I claim:

1. A new and distinct variety of *Angelonia* plant named 'ANGAF19273', as is herein illustrated and described.

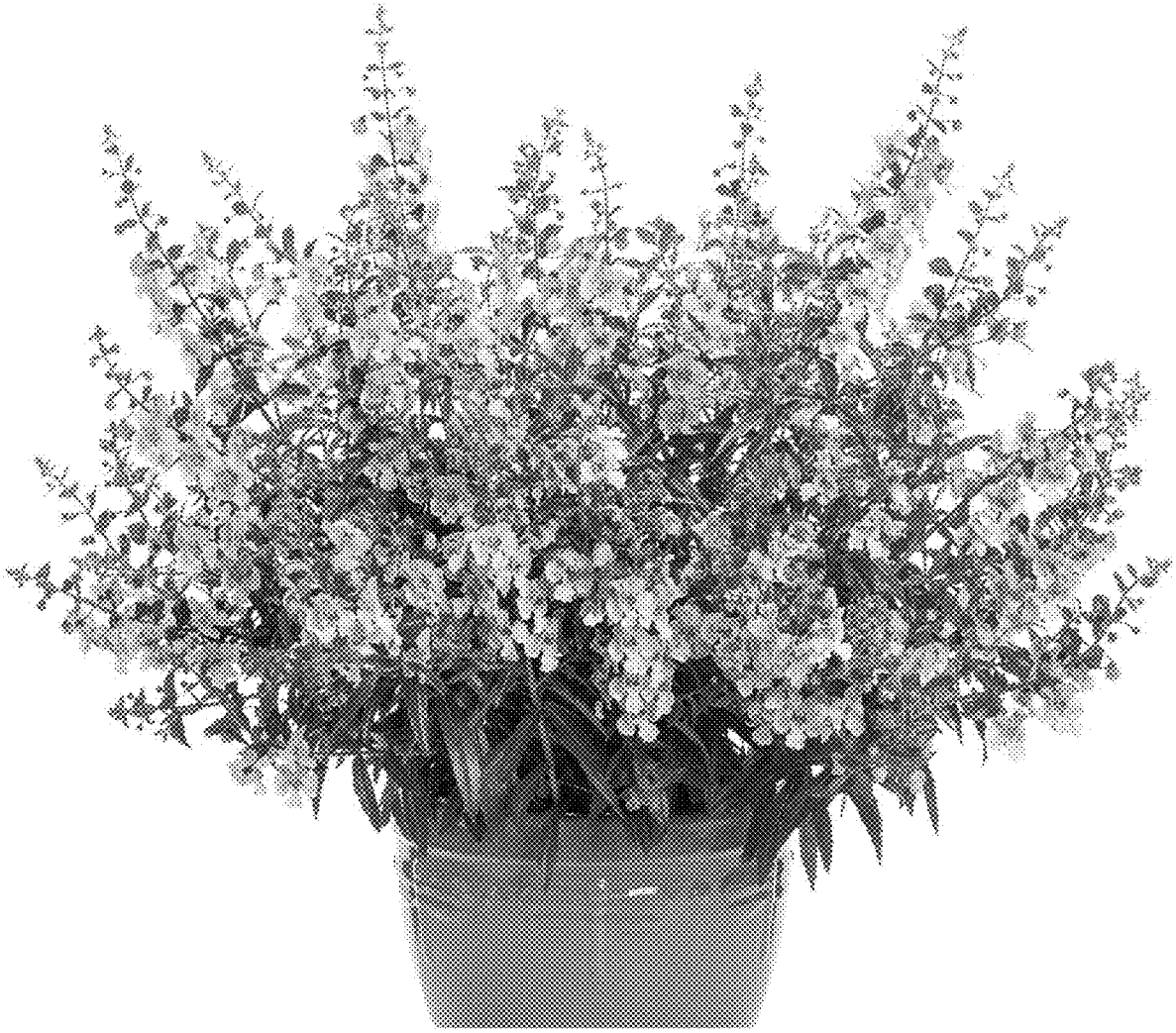

* * * * *